United States Patent
Kysilka et al.

(10) Patent No.: US 12,351,593 B2
(45) Date of Patent: Jul. 8, 2025

(54) PLATINUM IV COMPLEXES WITH SUBSTANTIALLY INCREASED ANTITUMOR EFFICACY

(71) Applicant: VUAB Pharma a.s., Roztoky (CZ)

(72) Inventors: Vladimír Kysilka, Prague (CZ); Jan Mengler, Prague (CZ); Miloš Mikoška, Bruntál (CZ)

(73) Assignee: VUAB PHARMA A.S., Roztoky (CZ)

( * ) Notice: Subject to any disclaimer, the term of this patent is extended or adjusted under 35 U.S.C. 154(b) by 758 days.

(21) Appl. No.: 17/640,056

(22) PCT Filed: Sep. 5, 2019

(86) PCT No.: PCT/EP2019/073686
§ 371 (c)(1),
(2) Date: Mar. 3, 2022

(87) PCT Pub. No.: WO2021/043402
PCT Pub. Date: Mar. 11, 2021

(65) Prior Publication Data
US 2022/0289781 A1    Sep. 15, 2022

(51) Int. Cl.
*C07F 15/00* (2006.01)
*A61P 35/00* (2006.01)

(52) U.S. Cl.
CPC .......... *C07F 15/0093* (2013.01); *A61P 35/00* (2018.01)

(58) Field of Classification Search
None
See application file for complete search history.

(56) References Cited

U.S. PATENT DOCUMENTS 6,503,943 B1    1/2003    Zak et al.

FOREIGN PATENT DOCUMENTS

| EP | 0328274 A1 | 8/1989 |
| RU | 2200164 C2 | 3/2003 |
| WO | 2014100417 A1 | 6/2014 |
| WO | 2016/34214 A1 | 3/2016 |

OTHER PUBLICATIONS

International Search Report issued in corresponding International Application No. PCT/EP2019/073686 dated May 12, 2020, pp. 1-3.
International Report on Patentability issued in corresponding International Application No. PCT/EP2019/073686 dated Aug. 28, 2020, pp. 1-13.
L.A. Durnov, et al., "Pediatric Oncology", Moscow Medicine Publishing House, Second Edition, pp. 1-4, 2002.
Russian Office Action issued in connection to International Application No. 2022108866 (English Translation Attached), (2023).
Search Report issued by the FIPS Russian Federation in connection with International Application No. PCT/EP2019/073686, dated Feb. 6, 2023 (English Translation Attached).
Kasparova J. et al, "Molecular Aspects of Antitumor Effects of a New Platinum(IV) Drug", Molecular Pharmacology, 2006, v. 70, No. 5, pp. 1708-1719.
Klaus Kummerer, "Pharmaceuticals in the Environment", Department of Environmental Health Sciences, Univ. of Medical Center Freiburg, Review in Advance, pp. 1-2, Aug. 18, 2010.

*Primary Examiner* — Nicole P Babson
(74) *Attorney, Agent, or Firm* — George Likourezos; Carter, DeLuca & Farrell LLP (57) ABSTRACT

Invention relates to new platinum (IV) complexes with substantially increased antitumor efficacy; a process for preparing these new platinum (IV) complexes; a pharmaceutical composition and a final dosage form for oral administration of the new platinum (IV) complexes; and the use of the new platinum (IV) complex in a method to treat a tumor disease, preferably a heavy-to-treat cancer, most preferably pancreatic cancer, preferably by oral administration.

12 Claims, 2 Drawing Sheets

PLATINUM IV COMPLEXES WITH SUBSTANTIALLY INCREASED ANTITUMOR EFFICACY

CROSS REFERENCE TO RELATED APPLICATIONS

The present application is a national stage application of International Application No. PCT/EP2019/073686, filed Sep. 5, 2019, the entire content of which is hereby incorporated by reference in its entirety.

FIELD OF THE INVENTION

Invention relates to new platinum (IV) complexes with substantially increased antitumor efficacy. A process for preparing said new platinum (IV) complexes is described. A pharmaceutical composition and a final dosage form for oral administration of the new platinum (IV) complexes is described. The use of the new platinum (IV) complex in a method to treat a tumor disease, preferably a heavy-to-treat cancer, most preferably pancreatic cancer, preferably by oral administration, is described.

BACKGROUND OF THE INVENTION

Cancer is a serious disease with continuous growth of incidence and prevalence. Despite significant advances in immunotherapy, cell therapy and biological therapy, there is still a continuing need for small molecules of anticancer drugs with enhanced antitumor efficacy, reduced toxicity, good availability and affordable price.

The platinum (II) complexes are long term used antitumor drugs. They have great antitumor efficacy, synergic effects in combination therapy, good availability and affordable price. The medically used platinum (II) complexes have planar structure with central $Pt^{2+}$ ion surrounded by two cis-neutral non-leaving amino-ligands and two cis-anionic leaving ligands $X_1$, $X_2$ as is illustrated in the Picture (I):

(I)

where $R_1$, $R_2$ is hydrogen or together 1R,2R-1,2-cyclohexyl and $X_1$, $X_2$ is chloride or together dicarboxylate. The great antitumor efficacy of platinum (II) complexes is based on a unique mechanism of action. Leaving ligands of platinum (II) complexes are substituted by water in intracellular space (process of "aquation") to form very reactive aqua-complexes that then react with DNA causing its deformation. Extensive damage of DNA structure induces a cascade of intracellular mechanisms leading to cell death (apoptosis).

In parallel, the cancer cell fights against such platinum (II) xenobiotics by converting them to inactive Pt-complexes, e.g. by means of metallothionein, methionine, glutathione etc. Inactivated Pt-complexes are then removed from the cell. The dependence between the structure of platinum (II) complexes and their antitumor activity was studied in articles [1]—Cleare M. J., Hoeschele J. D.: Platinum Metals Rev., Vol. 17, 2-13, 1973 and [2]—Ridgway H. J., Speer R. J. et al.: Journal of Clinical Hematology and Oncology, Vol. 7, No. 1, 220-230, 1976. The rate of "aquation" and the associated cytotoxicity and antitumor efficacy depend mainly on the strength of the bond between the leaving anion-ligand and the central platinum (II) ion. The weaker is this bond the faster is the formation of reactive aqua-complexes and the bigger is the associated toxicity and activity. The stronger this bond is the slower is the formation of reactive aqua-complexes and the less is associated toxicity and activity. Weakly bound conjugated bases of strong acids, e.g. nitrate or sulfate, were very reactive but they also caused severe toxicity (e.g. convulsions) and their testing had to be stopped. On the contrary, strongly bound conjugated bases of weak acids, e.g. $SCN^-$, $NO_2^-$, $CNO^-$ were nonreactive exhibiting marginal toxicity and activity only. The toxicity and antitumor efficacy are mutually inseparable in Pt (II) complexes due to both the same mechanism of action and low selectivity of action on tumor cells. Moderately bound anionic ligands as chlorides (Cisplatin) or dicarboxylates (Carboplatin, Oxaliplatin) have been developed for therapeutic use as a compromise between toxicity and antitumor efficacy of platinum (II) complexes. Their undesirable toxicity is then partially solved by premedication of patients; however, a problem of their serious toxicity remains.

Platinum (IV) complexes are prodrugs of platinum (II) complexes. They have occupied axial positions in their structure by other two anionic ligands, usually carboxylates. Axial ligands prevent the access of water to the central Pt ion and so, the necessary process of "aquation" can only take place after their reductive removal. Platinum (IV) complexes offer all advantages of platinum (II) complexes and concurrently improve both their stability and toxicity to healthy cells. An overview of the state of the art of platinum (IV) drugs is given in the reviews [3]—Johnston T. C., et al.: "The next Generation of Platinum Drugs: Targeted Pt (II) Agents, Nanoparticle Delivery and Pt (IV) Prodrugs", Chem. Rev. 2016, 116, 3436-3486] and [3]—Kenny R. G., et al.: "Platinum (IV) Prodrugs—A Step Closer to Ehrlich's Vision?", Eur. J. Inorg. Chem. 2017, 1596-1612. First promising lipophilic platinum (IV) complex for oral administration was discovered by Johnson Matthey, [4]—EP0328274, Johnson Matthey, priority 2 Feb. 1988. It has configuration cis-(ammine, cyclohexylamine)-trans-bis-acetate-cis-dichloride Pt(IV) and soon after, it entered clinical trials under the name Satraplatin. Although much effort has been made over the past 30 years to introduce Pt (IV) complexes into medical practice, it has not been achieved to the date.

The platinum (IV) complex TU31 with a geometric configuration cis-(ammine,1-adamantylamine)-trans-bis(1-adamantylcarboxylate)-cis-(dichloride) Pt (IV) of the formula (II) is a very promising platinum (IV) complex for therapy of cancer in the prior art:

(II)

(III)

wherein X is a conjugated anion of a strong mineral or organic acid.

In a preferred embodiment the ligand X is selected from the group consisting of nitrate, mesylate, monochloroacetate and trifluoroacetate.

In a preferred embodiment the ligand X is nitrate.

In a preferred embodiment the ligand X is mesylate.

In a preferred embodiment the ligand X is monochloroacetate.

In a preferred embodiment the ligand X is trifluoroacetate.

Without being bound by theory, the introduction of weakly bound conjugated anion of strong acid X to platinum (II) complexes is not possible due to big reactivity of Pt—X bond and big corresponding toxicity of subsequently formed aqua-platinum (II) species. However, the same introduction of weakly bound ligand X to the platinum (IV) complex TU31 can have a positive effect because reactive Pt—X bond is sterically shielded by bulky axial 1-adamantylcarboxylate ligands that are more difficult to remove in healthy cells unlike cancer cells. That results in suppression of toxicity of such platinum (IV) complex in healthy cells despite containing a highly reactive Pt—X bond. On the contrary, removal of shielding axial ligands in such platinum (IV) complex in cancer cells is enabled due to an increased concentration of protective reducing agents (e.g. metallothionein, glutathione), which is specific in cancer cells. That results in fast creation of toxic aqua-complexes of platinum (II) species in cancer cells with corresponding antitumor effect unlike healthy cells.

In a second aspect of the present invention, there is provided a method of preparing of a platinum (IV) complex of the formula (III) wherein X is a conjugated anion of a strong mineral or organic acid comprising the following steps of preparation:

a) Reacting of the starting platinum (IV) complex with the geometric configuration cis-(ammine,1-adamantylamine)-trans-bis(1-adamantylcarboxylate)-cis-(chloride, iodide) Pt (IV) (TU31-monoiodide) with stoichiometric excess of silver salt of strong acid, in the mixture of chlorinated hydrocarbon solvent, preferably chloroform, and corresponding strong acid at a boiling point of the solvent for reaction time necessary for conversion to obtain the mixture.

b) Removal of solid phase from the mixture by filtration to obtain the crude filtrate.

c) Washing the crude filtrate by water and drying the separated organic phase.

This platinum (IV) complex TU31 was discovered by VUAB Pharma, [5]-EP3189064, VUAB Pharma a.s., filed on 3 Sep. 2014. This platinum (IV) complex represents a combination of unique properties of 1-adamantyl ligands with the unique antitumor mechanisms of platinum (II) complexes. The introduction of three 1-adamantantyl ligands having properties of organic diamonds brings to the complex TU31 excellent stability, symmetry, compactness and penetration ability resulting in improved stability, cell uptake and antitumor efficacy. Reductive cleavage of axial bulky and symmetric 1-adamantylcarboxylate ligands needs increased level of cell defending reducing agents (e.g. metallothionein, methionine or glutathione) that is more specific for tumor cells unlike healthy cells. This makes it possible to suppress the toxicity in healthy cells unlike tumor cells. It was verified and confirmed in the preclinical stage of the complex TU31 where toxic symptoms were not even achieved by single oral administration of the complex TU31 both in rats and dogs.

However, the same lipophilicity, compactness and inertness results in a poor solubility of the complex TU31 in water that limits its bioavailability for the same reasons. This drawback was solved by reducing the particle size and by selecting a suitable vehicle, however, the limited bioavailability of the complex TU31 remains. It calls for the development of new derivatives of TU31 with further enhanced antitumor efficacy keeping advantages of the "mother" platinum (IV) complex TU31, mainly low toxicity and broad antitumor efficacy.

SUMMARY OF THE INVENTION

According to a first aspect of the invention, there is provided a platinum (IV) complex with geometric configuration cis-(ammine, 1-adamantylamine)-trans-bis(1-adamantylcarboxylate)-cis-(chloride, X) Pt (IV) of the general formula (III):

d) Removal of solvent from dried organic phase by evaporation to obtain the platinum (IV) complex of formula (III) wherein X is a conjugated anion of a strong mineral or organic acid.

In a preferred embodiment of the invention the method of preparing of a platinum (IV) complex of the general formula (III) wherein X is a conjugated anion of a strong mineral or organic acid further comprises step e) Dissolution of the platinum (IV) complex in acetone, addition of active carbon, ultrafiltration of the obtained suspension and precipitation of the obtained ultrafiltered solution of the pure platinum (IV) complex in abundance of water to obtain the pure platinum (IV) complex of the general formula (III) wherein X is a conjugated anion of a strong mineral or organic acid in nanoparticle size.

Figure 1:
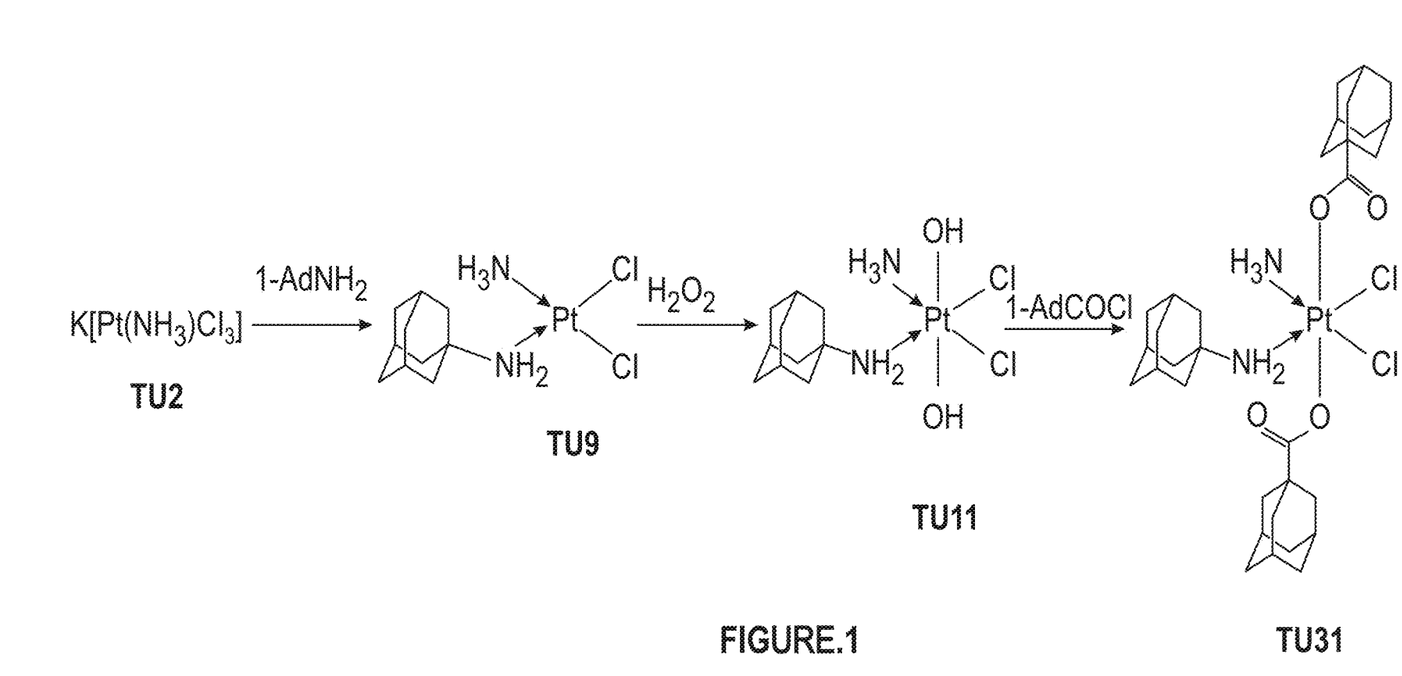
FIG. 1 a production scheme of platinum (IV) complex TU31.

The preferred preparing method according to the invention is introduction of weakly bound anion ligand X directly in the complex TU31 that is prepared according to FIG. 1.

It is preferred to introduce one iodide ligand instead of one chloride ligand in the starting TU31 complex in step a) to promote the conversion of the starting complex TU31 to the new platinum (IV) complex. The starting complex TU31-monoiodide with the geometric configuration cis-(ammine,1-adamantylamine)-trans-bis(1-adamantylcarboxylate)-cis-(chloride, iodide) Pt (IV), which corresponds to a platinum (IV) complex of the formula (III) wherein X is replaced by iodide, can be prepared by a three-step reaction procedure already known in the prior art. E.g. the chloride ligand can be replaced by iodide ligand in the platinum (II) complex TU9 intermediate (TU9—see FIG. 1) by reacting of the platinum (II) complex TU9 with stoichiometric amount of KI in water suspension at the temperature about 50° C. during 24 hours to obtain the platinum (II) complex TU9-monoiodide. The platinum (II) complex TU9-monoiodide is then oxidized to the corresponding platinum (IV) complex by the known procedure described e.g. in EP0328274, Johnson Mathey. Briefly, the Pt (II) complex TU9-monoiodide is oxidized by 30-50 stoichiometric excess of hydrogen peroxide at the temperature about 60° C. during 6-8 hours to obtain the platinum (IV) complex TU11-monoiodide (TU11—see the Scheme 1). Finally, the platinum (IV) complex TU11-monoiodide is esterified by excess of 1-adamantylcarbonyl chloride to obtain the starting complex TU31-monoiodide by the known procedure described e.g. in EP3189064, VUAB Pharma. Briefly, one stoichiometric equivalent of the complex TU11-monoiodide reacts with 5 stoichiometric equivalents of 1-adamantylcarbonyl chloride with corresponding amount of pyridine in 1,4-dioxane to obtain the crude complex TU31-monoiodide. The crude complex TU31-monoiodide is purified by repeated maceration in 1,4-dioxane and by water. The obtained product is then dissolved in acetone, active carbon is added, the suspension is ultrafiltered and the obtained ultrafiltered solution is precipitated in abundance of water to obtain the pure starting complex TU31-monoiodide.

In a preferred embodiment the yields of the new platinum (IV) complexes prepared according to the invention by the steps a) to e) range 62-78% with respect to the starting complex TU31-monoiodide. The purity of the obtained platinum (IV) complex is usually 96-98.5% (HPLC-UV).

In a preferred embodiment, the particle size of the obtained platinum (IV) complexes ranges from 100-300 nm measured by DLS (Dynamic Light Scattering) method.

The molecular weight of the obtained platinum (IV) complexes can be further confirmed by HPLC-MS method.

The preparing of the platinum (IV) complexes of the general formula (III) is explained in more detail in the Examples 1, 2 and 3.

According to a third aspect of the invention, there is provided a pharmaceutical composition comprising a platinum (IV) complex according to formula (III) with a pharmaceutically acceptable carrier.

In a preferred embodiment the pharmaceutical composition of a platinum (IV) complex according to formula (III) can be administered orally.

In a preferred embodiment the pharmaceutically acceptable carrier is a self-emulsifying vehicle, preferably stearoyl macrogol glycerides, most preferably Gelucire 50/13.

In a preferred embodiment the pharmaceutical composition comprises a platinum (IV) complex according to formula (III) in a nanoparticle size.

In a preferred embodiment there is provided a final dosage form for use in the therapy of tumor diseases, preferably for oral administration, comprising a pharmaceutical composition of the platinum (IV) complexes according to the invention, preferably in nanoparticle size, preferably with self-emulsifying vehicle, filled in acidoresistant capsules. The final dosage form according to the invention solves the problem of both the poor solubility with corresponding poor bioavailability of the new platinum (IV) complexes and instability of this complex in stomach and intestine where the concentration of reducing substances and other biodegrading agents is also increased, as in tumor cells. The conversion of the micro-particles of the platinum (IV) complexes of formula (III) to nanoparticles, preferably less than 250 nm, improves solubility and bioavailability of the new platinum (IV) complexes, preferably after oral administration.

Preparing of nanoparticles of the new platinum (IV) complexes is described in examples of preparing such platinum (IV) complexes.

In a preferred embodiment, the use of self-emulsifying vehicle in the composition, preferably stearoyl macrogol glycerides, most preferably Gelucire 50/13, supports both protection of the new platinum (IV) complexes against premature activation in intestine and bioavailability of this complex in the body by its encapsulation in vesicles. Gelucire 50/13 has a drop point about 50° C. and a low melt viscosity that enable easy preparing of the hot melt composition according to the present invention at temperature above 50° C. This vehicle is also relatively simple, cheap, non-toxic and certified for pharmaceutical uses.

In a preferred embodiment the mass portion of Gelucire 50/13 of at least 80 mass. % of the composition is recommended to ensure maximal supporting and protecting effects of this vehicle.

The use of acidoresistant capsules, according to a preferred embodiment, protects the new platinum (IV) complexes against premature activation in stomach after oral administration. The preferred acidoresistant capsules are hydroxypropylmethylcellulose-phtalate (HPMCP) or hydroxypropylmethylcellulose-acetate-succinate (HPMCAS) capsules which dissolve rapidly in the upper part of intestine unlike commonly used capsules with enteric coating. The platinum (IV) complex according to the invention must be protected as much as possible in the gastrointestinal system to avoid the risk of undesirable toxicity. This double protection of the new platinum (IV) complex by both acidoresistant capsule and self-emulsifying vehicle minimizes risk of its premature reduction/activation with accompanied toxicity until this complex reaches target cancer cells.

According to a fourth aspect of the invention there is provided a use of the new platinum (IV) complexes of the general formula (III) for use in a method to treat tumor diseases, preferably heavy-to-treat cancers, most preferably pancreatic cancers, by oral administration.

The present invention encompasses any one of the following aspects:

1) A platinum (IV) complex with geometric configuration cis-(ammine,1-adamantylamine)-trans-bis(1-adamantylcarboxylate)-cis-(chloride, X) Pt (IV) of the general formula (III):

wherein X is a conjugated anion of a strong mineral or organic acid.

2) The platinum (IV) complex according to aspect 1), wherein X is selected from the group consisting of nitrate, mesylate, monochloroacetate and trifluoroacetate.

3) A method of preparing a platinum (IV) complex according to aspects 1) or 2) comprising the following steps of preparation:

a) Reacting of the starting platinum (IV) complex with the geometric configuration cis-(ammine,1-adamantylamine)-trans-bis(1-adamantylcarboxylate)-cis-(chloride, iodide) Pt (IV) with stoichiometric excess of silver salt of strong acid, in the mixture of chlorinated hydrocarbon solvent, preferably chloroform, and corresponding strong acid at a boiling point of the solvent for reaction time necessary for conversion to obtain the mixture.

b) Removal of solid phase from the mixture by filtration to obtain the crude filtrate.

c) Washing the crude filtrate by water and drying the separated organic phase.

d) Removal of solvent from dried organic phase by evaporation to obtain the platinum (IV) complex according to aspect 1) or 2).

4) The method according to aspect 3) comprising a further step of:

e) Dissolution of the platinum (IV) complex in acetone, addition of active carbon, ultrafiltration of the obtained suspension and precipitation of the obtained ultrafiltered solution of the pure platinum (IV) complex in abundance of water to obtain the pure platinum (IV) complex according to aspect 1) or 2) in nanoparticle size.

5) A pharmaceutical composition of a platinum (IV) complex according to aspect 1) or 2), preferably for oral administration, comprising the Pt (IV) complex and a pharmaceutically acceptable carrier.

6) The pharmaceutical composition according to aspect 5), wherein the pharmaceutically acceptable carrier is a self-emulsifying vehicle, preferably stearoyl macrogol glycerides, most preferably Gelucire 50/13.

7) The pharmaceutical composition according to aspect 5) or 6), wherein the platinum (IV) complex is present in nanoparticle size.

8) The pharmaceutical composition according to aspect 6) or 7), wherein the mass portion of the self-emulsifying vehicle is greater than 80 mass. %.

9) The pharmaceutical composition according to any one of aspects 5) to 8), wherein the pharmaceutical composition is filled in acidoresistant capsules, preferably hydroxypropylmethylcellulose-phtalate or hydroxyperopylmethylcellulose-acetate-succinate capsules.

10) A platinum (IV) complex according to aspect 1) or 2) or a pharmaceutical composition according to any one of aspects 5) to 9) for use in a method to treat a tumor disease, preferably a heavy-to-treat cancer, most preferably pancreatic cancer, preferably by oral administration.

11) A method for treating tumor diseases, preferably heavy-to-treat cancer, most preferably pancreatic cancer, in a subject in need thereof comprising administering, preferably orally, the platinum (IV) complex according to aspect 1) or 2) or the pharmaceutical composition according to any one of aspects 5) to 9).

MORE DETAILED DESCRIPTION OF INVENTION

We surprisingly found that the platinum (IV) complexes of the general formula (III) have substantially improved antitumor efficacy with respect to the prior art. It is demonstrated in both in vitro and in vivo experiments. XTT method was used in the in vitro experiments. We tested mother platinum (IV) complex TU31 (where X=Cl⁻), three new platinum (IV) complexes according to the invention, where X=ClCH$_2$COO⁻ (complex TU105), F$_3$CCOO⁻ (complex TU106) and NO$_3^-$ (complex TU113), reference platinum (II) complex Oxaliplatin and reference platinum (IV) complex Satraplatin. Two cancer cell lines of heavy-to-treat tumors Capan-2 (pancreas adenocarcinoma) and PC-3 (prostate carcinoma) were used in XTT tests. The obtained results are summarized in the form of IC$_{50}$ values in the following Table 1:

TABLE 1

IC$_{50}$ values measured for new platinum (IV) complexes and reference platinum (II) complex Oxaliplatin

| Platinum complex tested | IC$_{50}$ μM | |
|---|---|---|
| | cancer cell line Capan-2 | cancer cell line PC-3 |
| Oxaliplatin (reference Pt (II) complex) | >100 | 55.7 |
| Satraplatin (reference Pt (IV)complex) | >30 | 10.2 |
| TU31 (mother Pt (IV) complex) | 0.60 | 0.91 |
| TU105 (new Pt (IV) complex) | 0.04 | 0.06 |
| TU106 (new Pt (IV) complex) | 0.02 | 0.07 |
| TU113 (new Pt (IV) complex) | 0.11 | 0.23 |

Capan-2 = pancreas adenocarcinoma, DSMZ, ACC-245
PC-3 = prostate carcinoma, ATCC ® CRL-1435 ™

We surprisingly found that the platinum (IV) complexes of the formula (III) have substantially increased antitumor efficacy in vitro with respect to the prior art. The mother complex TU31 has about 50 to 100 times better antitumor efficacy in vitro then the reference Oxaliplatin and 11 to 55 times better antitumor efficacy in vitro than reference Satraplatin. The excellent antitumor effects of the complex TU31 compared to the reference Oxaliplatin and Satraplatin, together with its very low toxicity and the possibility of oral administration, are good prerequisites for the success of the complex TU31 in the clinical trials. However, the new platinum (IV) complexes TU105, TU106 and TU113 of the general formula (III) according to the invention have $IC_{50}$ values even more than 1000 times better than reference Oxaliplatin, more than 100 times better than the reference Satraplatin and more than 15 times better than the mother complex TU31 for both cancer cell lines Capan-2 and PC-3. Such further improvement appears essential with respect to prior art and creates good preconditions for the further development of the new platinum (IV) complexes according to the invention, in particular for therapy of heavy-to-treat tumors, e.g. pancreatic tumors.

More detailed information on the performance and results of XTT tests is given in the Example 4.

Two new platinum (IV) complexes TU105 and TU106 from XTT tests were further studied in vivo on athymic mice model with two pancreatic tumors. The platinum (IV) complex Satraplatin and mother complex TU31 were used as reference compounds again. Two heavy-to-treat tumors of pancreas Capan-2 and PaTu8902 were cultivated and then subcutaneously administered to mice at a dose of $1.10^7$ cells/mouse. After an increase in the subcutaneous tumors to a volume of about 0.2 cm$^3$, two doses of respective complexes 2×20 mg/kg were administered orally every 1 week. Control group of mice received no drug. Volume of tumors were continuously measured throughout the experiment. Three weeks after the second dose, mice were sacrificed, tumors removed, weighed and obtained data were evaluated in the form of tumor volume inhibition in % (TVI %) and tumor weight inhibition in % (TWI %), where:

TVI %=100−[(TVexp/TVcont)×100]

TVexp=average volume of cured tumors in cm$^3$
TVcont=average volume of control tumors in cm$^3$ TWI %=100−[(TWexp/TWcont)×100]

TWexp=average weight of cured tumors in g
TWcont=average weight of control tumors in g The obtained results are summarized in the Table 2 and Table 3.

TABLE 2

Results of antitumor efficacy of platinum (IV) complexes TU31, TU105, TU106 in %
TWI, single oral dose 20 mg/kg, duration of the experiment 28 days (28 d)
Mouse: Athymic Nude-FOXN-1$^{nu}$, 6 mice per group (3 male + 3 female)
Tumor: Capan-2, pancreas adenocarcinoma (DSMZ, ACC-245)

| Pt (IV) complex | Average tumor volume during experiment in days (d), in cm$^3$ | | | | | | | | | TVI % | Average tumor weight in g 28 d | TWI % |
|---|---|---|---|---|---|---|---|---|---|---|---|---|
| | 1 d | 4 d | 8 d | 11 d | 15 d | 18 d | 22 d | 25 d | 29 d | | | |
| Control | 0.20 | 0.27 | 0.35 | 0.44 | 0.53 | 0.63 | 0.73 | 0.85 | 1.00 | — | 0.793 | — |
| Satraplatin | 0.21 | 0.23 | 0.30 | 0.39 | 0.47 | 0.56 | 0.66 | 0.77 | 0.90 | 10.0 | 0.711 | 10.3 |
| TU31 | 0.21 | 0.23 | 0.27 | 0.31 | 0.37 | 0.43 | 0.49 | 0.56 | 0.63 | 37.0 | 0.371 | 53.2 |
| TU105 | 0.20 | 0.21 | 0.22 | 0.23 | 0.27 | 0.30 | 0.34 | 0.37 | 0.40 | 60.0 | 0.213 | 73.1 |
| TU106 | 0.21 | 0.21 | 0.23 | 0.24 | 0.25 | 0.26 | 0.28 | 0.29 | 0.31 | 69.0 | 0.166 | 79.1 |

TABLE 3

Results of antitumor efficacy of platinum (IV) complexes TU31, TU105, TU106 in %
TWI, single oral dose 20 mg/kg, duration of the experiment 28 days (28 d)
Mouse: Athymic Nude-FOXN-1$^{nu}$, 6 mice per group (3 male + 3 female)
Tumor: PaTu8902, pancreas adenocarcinoma, metastatic, grade II (DSMZ, ACC-179)

| Pt (IV) complex | Average volume of tumor during experiment in days (d), in cm$^3$ | | | | | | | | | TVI % | Average tumor weight in g 28 d | TWI % |
|---|---|---|---|---|---|---|---|---|---|---|---|---|
| | 1 d | 4 d | 8 d | 11 d | 15 d | 18 d | 22 d | 25 d | 29 d | | | |
| Control | 0.21 | 0.58 | 1.15 | 2.20 | 3.59 | 5.44 | 7.79 | 10.59 | 13.65 | — | 8.186 | — |
| Satraplatin | 0.21 | 0.50 | 0.99 | 1.94 | 3.10 | 4.80 | 6.80 | 9.35 | 11.90 | 12.8 | 7.245 | 11.5 |
| TU31 | 0.21 | 0.28 | 0.54 | 0.86 | 1.44 | 2.27 | 3.35 | 4.62 | 5.96 | 56.3 | 4.017 | 50.9 |
| TU105 | 0.21 | 0.21 | 0.40 | 0.62 | 1.06 | 1.65 | 2.46 | 3.40 | 4.35 | 68.1 | 2.522 | 69.2 |
| TU106 | 0.21 | 0.21 | 0.37 | 0.60 | 1.01 | 1.60 | 2.35 | 3.27 | 4.20 | 69.2 | 2.317 | 71.7 |

It follows from obtained results that the mother complex TU31 has very good antitumor efficacy in both pancreatic tumors having TWI equal to about 50% unlike of the reference complex Satraplatin. However, the new platinum (IV) complexes TU105 and TU106 according to the invention demonstrated a significantly improved anti-tumor efficacy expressed in TWI % equal to about 70-80% that is about 7 times greater than for the reference platinum (IV) complex Satraplatin and significantly greater than for the mother complex TU31, too for both studied pancreatic tumors. More detailed information on the performance and results of the in vivo tests on athymic mice model is given in the Example 5.

The results achieved from both in vitro and in vivo tests confirm a substantially improved antitumor efficacy of the new platinum (IV) complexes with respect to the prior art. The new platinum (IV) complexes of the general formula (III) according to the invention offer very promising and price affordable tools for oral therapy of cancer, preferably heavy-to-treat cancers, more preferably pancreatic cancers. The broad anti-tumor efficacy of the new platinum (IV) complexes according to the invention is based on the known and unique mechanism of action of the platinum (II) metabolites, which little depends on the variation of signaling pathways and tumor markers in the cells. In this case, the problem of a drug targeting of the toxic complexes is solved by the selective activation of the platinum (IV) complex in tumor cells according to the invention.

The invention is further explained and illustrated, but not limited, by the following examples and figures.

The figures show

EXAMPLES

Example 1

Preparing cis-(ammine,1-adamantylamine)-trans-bis (1-adamantylcarboxylate)-cis-(chloride, monochloroacetate) Pt (IV), the new Pt(IV) complex TU105, molecular weight 850.77 g/mol Preparing procedure was carried out in a fume hood in the absence of light. The starting Pt (IV) complex TU31-monoiodide was prepared according to the prior art.

70 mg of silver oxide (0.3 mmol) and 7.9 g of monochloroacetic acid (83.6 mmol) were stirred in 20 ml of chloroform 1 hour at room temperature. 360 mg of the starting Pt (IV) complex-monoiodide (0.4 mmol) is then added and the mixture is stirred 6 hours at 63° C. (mild reflux). Obtained suspension was cooled to room temperature and a solid phase was then removed by filtration. The obtained organic solution was extracted three times by 20 ml water to remove water soluble compounds from the organic solution. The washed organic solution was dried by means of molecular sieves and chloroform was then removed from the clear dried solution by vacuum distillation to obtain crude complex TU105. The crude complex TU105 was dissolved in 33 ml acetone and 20 mg of active carbon was added to obtain suspension that was stirred 0.5 hour at room temperature. The suspension was then ultrafiltered through a filter with porosity 0.22 µm to obtain ultrafiltered solution of the product that was then precipitated in 100 ml cold water to obtain 270 mg of the pure complex TU105, yield 78% theory, the purity 98.1% (HPLC method) and particle size 200-400 nm (DLS method). MS spectrometry confirms molecular weight.

Example 2

Preparing cis-(ammine,1-adamantylamine)-trans-bis (1-adamantylcarboxylate)-cis-(chloride, trifluoroacetate) Pt (IV), the new Pt(IV) complex TU106, molecular weight 870.30 g/mol Preparing procedure was carried out in a fume hood in the absence of light. The starting Pt (IV) complex TU31-monoiodide was prepared according to the prior art.

The mixture of 360 mg of the starting Pt (IV) complex-monoiodide (0.4 mmol), 135 mg of silver salt of trifluoroacetic acid (0.6 mmol), 9.6 g of trifluoroacetic acid (84.2 mmol) and 20 ml of chloroform was stirred 6 hours at 63° C. (mild reflux). Obtained suspension was cooled to room temperature and a solid phase was then removed by filtration. The obtained organic solution was extracted three times by 20 ml water to remove water soluble compounds from the organic solution. The washed organic solution was dried by means of molecular sieves and chloroform was then removed from the clear dried solution by vacuum distillation to obtain crude complex TU106. The crude complex TU106 was dissolved in 33 ml acetone and 20 mg of active carbon was added to obtain suspension that was stirred 0.5 hour at room temperature. The suspension was then ultrafiltered through a filter with porosity 0.22 µm to obtain ultrafiltered solution of the product that was then precipitated in 100 ml cold water to obtain 287 mg of the pure complex TU106, yield 81% theory, the purity 98.5% (HPLC method) and particle size 200-400 nm (DLS method). MS spectrometry confirmed molecular weight.

Example 3

Preparing cis-(ammine,1-adamantylamine)-trans-bis (1-adamantylcarboxylate)-cis-(chloride, nitrate) Pt (IV), the new Pt(IV) complex TU113, molecular weight 819.29 g/mol Preparing procedure was carried out in a fume hood in the absence of light. The starting Pt (IV) complex TU31-monoiodide was prepared according to the prior art.

The mixture of 360 mg of the starting Pt (IV) complex-monoiodide (0.4 mmol), 100 mg of AgNO$_3$ (0.6 mmol), 6 ml (8.46 g) of nitric acid 65% (87.3 mmol) and 20 ml of chloroform was stirred 10 hours in at 63° C. (mild reflux). Obtained suspension was cooled to room temperature and a solid phase was then removed by filtration. From the filtrate, the organic phase was separated from the aqueous phase of HNO$_3$. The obtained organic phase was extracted three times by 20 ml water to remove water soluble compounds from the organic solution. The washed organic solution was dried by means of molecular sieves and chloroform was then removed from the clear dried solution by vacuum distillation to obtain crude complex TU113. The crude complex TU113 was dissolved in 33 ml acetone and 20 mg of active carbon was added to obtain suspension that was stirred 0.5 hour at room temperature. The suspension was then ultrafiltered through a filter with porosity 0.22 µm to obtain ultrafiltered solution of the product that was then precipitated in 100 ml cold water to obtain 227 mg of the pure complex TU113, yield 69% theory, the purity 96.2% (HPLC method) and particle size 200-350 nm (DLS method). MS spectrometry confirms molecular weight.

Example 4

Study of Antitumor Efficacy in Vitro of the New Pt(IV) Complexes According to the Present Invention, Heavy to Treat Tumors of Pancreas and Prostate, XTT Test Antitumor efficacy of the new Pt(IV) complexes according to the invention was studied on heavy to treat cancer lines of pancreas and prostate. XTT method was used. Results were evaluated in $IC_{50}$ values and compared with reference Pt(II) complex Oxaliplatin and reference Pt (IV) complex Satraplatin.

Tested Compounds:
1. Reference Pt (II) complex Oxaliplatin, (1R,2R-1,2-cyclohexanediamine-N,N') (ethanedioato-O,O') platinum (II), CAS No.: 61825-94-3, purity: 99.7% (HPLC), source VUAB Pharma a.s.
2. Reference Pt (IV) complex Satraplatin, cis-(ammine, cyclohexylamine)-trans-bis-acetate-cis-dichloride Pt(IV), CAS No. 129580-63-8, >98.8% (HPLC), source WATSON Inc., Ltd, CN.
3. Mother Pt (IV) complex TU31, cis-(ammine,1-adamantylamine)-trans-bis(1-adamantylcarboxylate)-cis-(dichloride) Pt (IV), CAS No.: NCE, purity 99.5% (HPLC), source VUAB Pharma a.s.
4. The new Pt (IV) complex TU105, cis-(ammine,1-adamantylamine)-trans-bis(1-adamantylcarboxylate)-cis-(chloride, monochloroacetate) Pt (IV), CAS No.: NCE, purity 98.1% (HPLC), source VUAB Pharma a.s.
5. The new Pt (IV) complex TU106, cis-(ammine,1-adamantylamine)-trans-bis(1-adamantylcarboxylate)-cis-(chloride, trifluoroacetate) Pt (IV), CAS No.: NCE, purity 98.5% (HPLC), source VUAB Pharma a.s.
6. The new Pt (IV) complex TU113, cis-(ammine,1-adamantylamine)-trans-bis(1-adamantylcarboxylate)-cis-(chloride, nitrate) Pt (IV), CAS No.: NCE, purity 96.2% (HPLC), source VUAB Pharma a.s.

Cancer Cell Lines:
Fresh tumor cell lines were purchased from the Cell Bank to ensure their quality and activities.
  a) Capan-2, pancreatic ductal adenocarcinoma, DSMZ, ACC-245
  b) PC-3, prostate carcinoma, ATCC® CRL1435™

Cultivation's Conditions of Tumor Cell Lines:
Abbreviation of Used Compounds:
  DMSO: dimethyl sulfoxide
  PBS: phosphate buffered saline
  XTT: 2,3-bis-(2-methoxy-4-nitro-5-sulphophenyl)-2H-tetrazolium-5-carboxanilide salt
  PMS: N-methyl-dibenzopyrazinmethylsulfate
  FBS: fetal bovine serum
  NEAA: non-essential amino acids
  L-glu: L-glutamine
  DMEM: Dulbecco's Modified Eagle's Medium (SigmaAldrich)
  PMS: phenazine methosulfate
  Cultivation's conditions: 37° C., 5% $CO_2$
  Growth medium: DMEM, 10% FBS, 2 mM L-glut., NEAA 100×

XTT Working Procedure:
Tested compounds were dissolved in DMSO and diluted by PBS to tested concentration range just before addition to cell lines in wells. PBS was used as a positive control, DMSO in final concentration 20% was used as a negative control. All concentrations of compounds were assayed in triplicates. Each determination was carried out twice and was blinded for experimenter.

Testing was conducted on a 96-well plate. Dosage of tumor cells was about 2.5. $10^4$ cells per well, dosage of growth medium was 100 μl per well. After 24 hours, the growth medium was suck off and 80 μl of fresh growth medium and 20 μl of solution with different concentration of the tested substance were added to wells. After 72 hours, the medium was suck off and 100 μl of a solution of Optimem reagent containing XTT and PMS were added to wells. After another 4 hours, the absorbance was measured at 450 nm (reference was at 630 nm). Results as $IC_{50}$ were evaluated from the graph of normalized viability of cells plotted against the logarithm of the concentration of the substance.

The Obtained Results:
Results are summarized in the Table 1:

TABLE 1

Measured $IC_{50}$ values for the new Pt (IV) complexes and reference Pt (II) complex Oxaliplatin.

| | $IC_{50}$ μM | |
| --- | --- | --- |
| Platinum complex tested | cancer cell line Capan-2 | cancer cell line PC-3 |
| Oxaliplatin (reference Pt (II) complex) | >100 | 55.7 |
| Satraplatin (reference Pt (IV)complex) | >30 | 10.2 |
| TU31 (mother Pt (IV) complex) | 0.60 | 0.91 |
| TU105 (new Pt (IV) complex) | 0.04 | 0.06 |
| TU106 (new Pt (IV) complex) | 0.02 | 0.07 |
| TU113 (new Pt (IV) complex) | 0.11 | 0.23 |

Conclusion to Anticancer Efficacy in Vitro of the New Pt (IV) Complexes:

The mother complex TU31 has about 50 to 100 times better antitumor efficacy in vitro then the reference Oxaliplatin and 11 to 55 times better antitumor efficacy in vitro than reference Satraplatin. The excellent antitumor effects of the complex TU31 compared to the reference Oxaliplatin and Satraplatin, together with its very low toxicity and the possibility of oral administration, are good prerequisites for the success of the complex TU31 in the clinical trials.

However, the new Pt (IV) complexes TU105, TU106 and TU113 according to the invention have $IC_{50}$ values even more than 1000 times better than reference Oxaliplatin, more than 100 times better than the reference Satraplatin and more than 15 times better than the mother complex TU31 for both cancer cell lines Capan-2 and PC-3. Such improvement of the new Pt (IV) complexes according to the invention appears essential with respect to prior art.

Example 5

Study of Antitumor Efficacy in Vivo of the New Pt(IV) Complexes According to the Present Invention, Two Heavy to Treat Tumors of Pancreas, Athymic Mice Model In vivo model: Athymic Nude-FOXN-1$^{nu}$, 6 mice per group (3 male+3 female)
Cancer Cell Lines Used:
  a) Capan-2, pancreatic adenocarcinoma, ductal (DSMZ, ACC-245)

b) PaTu9802, pancreatic adenocarcinoma, ductal, high metastatic, grade II (DSMZ, ACC-179)

Used Pt (IV) Complexes:
  a) the reference Pt (IV) complex Satraplatin, detailed specification, see example 4.
  b) the mother Pt (IV) complex TU31, detailed specification, see example 4.
  c) the new Pt (IV) complex TU105, detailed specification, see example 4.
  d) the new Pt (IV) complex TU106, detailed specification, see example 4.

Used Doses for Oral Administration:

The homogenous bulk composition of the each tested Pt (IV) complex (20 mass. %) with Gelucire 50/13 (80 mass. %) was converted to water emulsion before oral administration to mice.

Cultivation conditions of cancer cell lines: 37° C., 5% $CO_2$, DMEM (Dulbecco's Modified Eagle's Medium, Sigma Aldrich), 10% FBS, (fetal bovine serum), 2 mM L-glutamin, non-essential aminoacids Transplantation of cancer cells: A dose $1 \times 10^7$ of cells was subcutaneously transplanted to each experimental mouse, then mice were subdivided into individual experimental groups. Each experimental group has a control group that do did not receive the drug.

Test Execution:

After an increase in the subcutaneous tumors to a volume of about 0.2 cm$^3$, two doses of respective complexes 2×20 mg/kg were administered orally every 1 week. The control group of mice received no drug. Volume of tumors were continuously measured throughout the experiment. Three weeks after the second dose, mice were sacrificed, tumors removed, weighed and obtained data were evaluated in the form of tumor volume inhibition in % (TVI %) and tumor weight inhibition in % (TWI %), where:

$$TVI \% = 100 - [(TVexp/TVcont) \times 100]$$

TVexp=average volume of cured tumors in cm$^3$
TVcont=average volume of control tumors in cm$^3$ $$TWI \% = 100 - [(TWexp/TWcont) \times 100]$$

TWexp=average weight of cured tumors in g
TWcont=average weight of control tumors in g Obtained Results:

The obtained results are summarized in the Table 2 and Table 3.

TABLE 2

Results of antitumor efficacy of Pt (IV) complexes TU31, TU105, TU106 in %
TWI, single oral dose 20 mg/kg, duration of the experiment 28 days (28 d)
Tumor: Capan-2, pancreatic adenocarcinoma (DSMZ, ACC-245)

| Pt (IV) complex | Average tumor volume during experiment in days (d), in cm³ | | | | | | | | | TVI % | Average tumor weight in g 28 d | TWI % |
|---|---|---|---|---|---|---|---|---|---|---|---|---|
| | 1 d | 4 d | 8 d | 11 d | 15 d | 18 d | 22 d | 25 d | 29 d | | | |
| Control | 0.20 | 0.27 | 0.35 | 0.44 | 0.53 | 0.63 | 0.73 | 0.85 | 1.00 | — | 0.793 | — |
| Satraplatin | 0.21 | 0.23 | 0.30 | 0.39 | 0.47 | 0.56 | 0.66 | 0.77 | 0.90 | 10.0 | 0.711 | 10.3 |
| TU31 | 0.21 | 0.23 | 0.27 | 0.31 | 0.37 | 0.43 | 0.49 | 0.56 | 0.63 | 37.0 | 0.371 | 53.2 |
| TU105 | 0.20 | 0.21 | 0.22 | 0.23 | 0.27 | 0.30 | 0.34 | 0.37 | 0.40 | 60.0 | 0.213 | 73.1 |
| TU106 | 0.21 | 0.21 | 0.23 | 0.24 | 0.25 | 0.26 | 0.28 | 0.29 | 0.31 | 69.0 | 0.166 | 79.1 |

TABLE 3

Results of antitumor efficacy of Pt (IV) complexes TU31, TU105, TU106 in %
TWI, single oral dose 20 mg/kg, duration of the experiment 28 days (28 d)
Tumor: PaTu8902, pancreatic adenocarcinoma, metastatic, grade II (DSMZ, ACC-179)

| Pt (IV) complex | Average volume of tumor during experiment in days (d), in cm³ | | | | | | | | | TVI % | Average tumor weight in g 28 d | TWI % |
|---|---|---|---|---|---|---|---|---|---|---|---|---|
| | 1 d | 4 d | 8 d | 11 d | 15 d | 18 d | 22 d | 25 d | 29 d | | | |
| Control | 0.21 | 0.58 | 1.15 | 2.20 | 3.59 | 5.44 | 7.79 | 10.59 | 13.65 | — | 8.186 | — |
| Satraplatin | 0.21 | 0.50 | 0.99 | 1.94 | 3.10 | 4.80 | 6.80 | 9.35 | 11.90 | 12.8 | 7.245 | 11.5 |
| TU31 | 0.21 | 0.28 | 0.54 | 0.86 | 1.44 | 2.27 | 3.35 | 4.62 | 5.96 | 56.3 | 4.017 | 50.9 |
| TU105 | 0.21 | 0.21 | 0.40 | 0.62 | 1.06 | 1.65 | 2.46 | 3.40 | 4.35 | 68.1 | 2.522 | 69.2 |
| TU106 | 0.21 | 0.21 | 0.37 | 0.60 | 1.01 | 1.60 | 2.35 | 3.27 | 4.20 | 69.2 | 2.317 | 71.7 |

Figure 2:
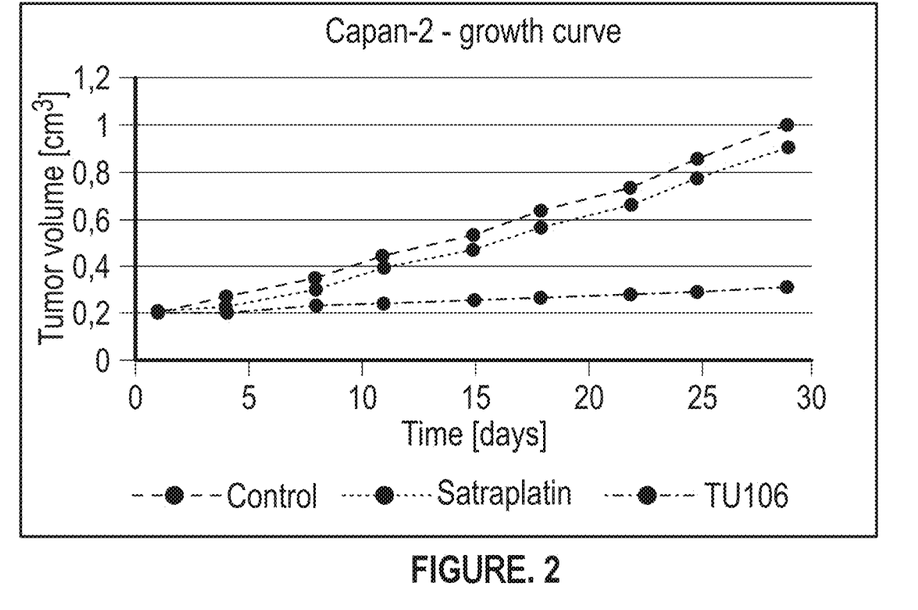
FIG. 2 a tumor grow curve of Capan-2.
Figure 3:
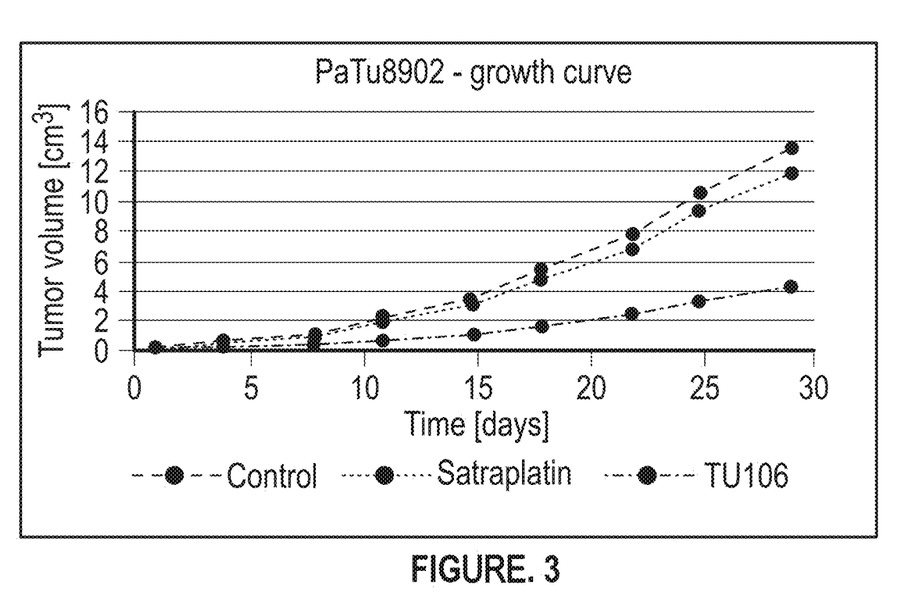
FIG. 3 a tumor grow curve of PaTu8902.

Achieved results in the Tables 2 and 3 are further illustrated in the tumor grow curves for both pancreatic tumors in FIGS. 2 and 3.

Conclusion to Anticancer Efficacy in Vivo of the New Pt (IV) Complexes According to the Invention, Athymic Mice Model:

The new Pt (IV) complexes TU105 and TU106 according to the invention demonstrated a significantly improved antitumor efficacy expressed both in TVI % and TWI % equal to about 70-80% that is about 7 times greater than for the reference Pt (IV) complex Satraplatin and substantially greater than for the mother complex TU31, too, for both studied heavy to treat pancreatic tumors. The results achieved confirm a substantially improved antitumor efficacy of the new Pt (IV) complexes according to the invention with respect to the prior art. The new Pt (IV) complexes of the general formula (III) according to the invention offer very promising and price affordable tool for oral therapy of cancer, preferably heavy-to-treat cancers, more preferably pancreatic cancers.

The invention claimed is:

1. A platinum (IV) complex with geometric configuration cis-(ammine, 1-adamantylamine)-trans-bis(1-adamantylcarboxylate)-cis-(chloride, X) Pt (IV) of the general formula (III):

wherein X is selected from the group consisting of nitrate, mesylate, monochloroacetate and trifluoroacetate.

2. A platinum (IV) complex according to claim 1 for use in a method to treat a tumor disease by oral administration.

3. A pharmaceutical composition of a platinum (IV) complex according to claim 1, comprising the Pt (IV) complex and a pharmaceutically acceptable carrier.

4. The pharmaceutical composition according to claim 3, wherein the pharmaceutically acceptable carrier is a self-emulsifying vehicle, wherein the self-emulsifying vehicle is stearoyl macrogol glycerides.

5. The pharmaceutical composition according to claim 3, wherein the platinum (IV) complex is present in nanoparticle size.

6. The pharmaceutical composition according to claim 4, wherein the mass portion of the self-emulsifying vehicle is greater than 80 mass. %.

7. The pharmaceutical composition according to claim 3, wherein the pharmaceutical composition is filled in acidoresistant capsules, wherein the acidoresistant capsules are hydroxypropylmethylcellulose-phtalate or hydroxyperopylmethylcellulose-acetate-succinate capsules.

8. A pharmaceutical composition according to claim 3 for use in a method to treat a tumor disease by oral administration.

9. A method of preparing a platinum (IV) complex according to claim 1 comprising the following steps of preparation:
   a) Reacting a starting platinum (IV) complex with the geometric configuration cis-(ammine, 1-adamantylamine)-trans-bis(1-adamantylcarboxylate)-cis-(chloride, iodide) Pt (IV) with stoichiometric excess of silver salt of strong acid, in a mixture of chlorinated hydrocarbon solvent, and corresponding strong acid at a boiling point of the solvent for reaction time necessary for conversion to obtain the mixture;
   b) Removal of solid phase from the mixture by filtration to obtain a crude filtrate;
   c) Washing the crude filtrate by water and drying a separated organic phase; and
   d) Removal of solvent from the dried organic phase by evaporation to obtain the platinum (IV) complex according to claim 1.

10. The method according to claim 9 comprising a further step of:
    e) Dissolution of the platinum (IV) complex in acetone, addition of active carbon, ultrafiltration of an obtained suspension and precipitation of an obtained ultrafiltered solution of the pure-platinum (IV) complex in abundance of water to obtain a pure platinum (IV) complex according to claim 1 in nanoparticle size.

11. A method for treating a tumor disease by oral administration the platinum (IV) complex according to claim 1 to a subject in need.

12. A method for treating a tumor disease by oral administration a pharmaceutical composition according to claim 3 to a subject in need.

* * * * *